(12) United States Patent
Gresser et al.

(10) Patent No.: US 6,419,945 B1
(45) Date of Patent: *Jul. 16, 2002

(54) BUFFERED RESORBABLE INTERNAL FIXATION DEVICES AND METHODS FOR MAKING MATERIAL THEREFORE

(75) Inventors: Joseph D. Gresser, Brookline; Debra J. Trantolo, Princeton; Robert Langer; Alexander M. Klibanov, both of Newton; Donald L. Wise, Belmont, all of MA (US)

(73) Assignee: Cambridge Scientific, Inc., Belmont, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/166,508

(22) Filed: Oct. 5, 1998

Related U.S. Application Data

(63) Continuation-in-part of application No. 08/626,521, filed on Apr. 3, 1996, now Pat. No. 5,817,328, which is a continuation-in-part of application No. 08/587,616, filed on Jan. 17, 1996, now abandoned.

(51) Int. Cl.[7] ................................................. A61F 2/02
(52) U.S. Cl. ................ 424/426; 514/772.1; 514/772.3; 514/772.4
(58) Field of Search .................. 424/426; 514/772.1, 514/772.3, 772.4

(56) References Cited

U.S. PATENT DOCUMENTS

| 5,741,329 A | 4/1998 | Agrawal et al. ............... 623/11 |
| 5,817,328 A | * 10/1998 | Gresser et al. ............... 424/426 |
| 5,981,619 A | 11/1999 | Shikinami et al. .......... 523/113 |

OTHER PUBLICATIONS

Shikinami et al., "Bioresorbable Devices Made of Groged Composites of Hydroxyapatite (HA) Particles and Poly–L–lactide (PLLA): Part I. Basic Characteristics", Biomaterial 20: 859–877 (1999).

* cited by examiner

Primary Examiner—Carlos A. Azpuru
(74) Attorney, Agent, or Firm—Weingarten, Schurgin, Gagnebin & Hayes LLP

(57) ABSTRACT

An internal fixation device and a bioerodible implantable material useful therefor comprise a bioerodible polymer that produces acidic products or low molecular weight resorbable fragments upon hydrolytic degradation, and a buffering or neutralizing agent in sufficiently high concentration to moderate the rate of change of pH of said bioerodible material during bioerosion. The buffering or neutralizing agent acts to reduce the inflammatory foreign body response generated by the acidic products and reduces the sterile abscess condition that occurs at the site of the bioerodible implant materials of the prior art. Internal fixation devices (IFDs) according to the invention are useful, for example, for the repair, replacement or reconstruction of damaged bone in any area of the body.

24 Claims, 2 Drawing Sheets

BUFFERED RESORBABLE INTERNAL FIXATION DEVICES AND METHODS FOR MAKING MATERIAL THEREFORE

CROSS-REFERENCE TO RELATED APPLICATIONS

This application is a continuation-in-part of U.S. application Ser. No. 08/626,521, now U.S. Pat. No. 5,817,328, filed Apr. 3, 1996 which is a continuation-in-part of U.S. application Ser. No. 08/587,616, filed Jan. 17, 1996, now abandoned, the whole of which are hereby incorporated by reference herein.

STATEMENT REGARDING FEDERALLY SPONSORED RESEARCH OR DEVELOPMENT

Not applicable

BACKGROUND OF THE INVENTION

The trend in internal fixation devices for repair of damaged bone is toward the use of resorbable, tissue compatible biopolymers. Biopolymers such as poly(glycolic acid) (PGA), poly(lactide) (PLA), and copolymers of lactic and glycolic acids, (poly(lactide-co-glycolide) or PLGA) have been used in the production of internal fixation devices, such as screws, pins, and rods to hold bone together following surgery, or to repair broken bones. Other polymers, such as poly(dioxanone), have also been considered for use in the manufacture of surgical internal fixation devices. However, it has been observed that tissue response to resorbable implants fabricated from these biopolymers is not uniformly acceptable (Bostman, J. Bone and Joint Surg. 73, 148–153 (1991)).

The tissue response to biopolymer-based implants has been well documented. Late sterile inflammatory foreign body response (sterile abscess) has been reported in about 8% of fractures repaired with these polymers (Bostman, supra). In a randomized study of 56 open reduction and internal fixation of malleolar fractures of the ankle with metal ASIF screws and plates or with rods of PLGA, two cases of sterile inflammatory wound sinus were observed 3 to 4 months after the operation in the injuries fixed with the polymer rods (Rokkanen et al., Lancet 1, 1422–1425 (1985); Bostman et al., J. Bone and Joint Surg., 69-B(4), 615–619 (1987)). Other studies have also documented an inflammatory reaction following implantation of PGA or PLGA fixation devices. The fraction of patients suffering from this reaction ranges from 4.6 to 22.5% (Bostman et al., Clin. Orthop. 238, 195–203 (1989); Bostman et al., Internat. Orthop. 14, 1–8 (1990); Hirvensalo et al., Acta Orthop. Scandinavica, Supplementum 227, 78–79 (1988); Hoffman et al., Unfallchirurgie 92, 430–434 (1989); Partio et al., Acta Orthop. Scandinavica, Supplementum 237, 43–44 (1990); Bostman et al., Internat. Orthop. 14, 1–8 (1990)). The inflammatory reaction is not limited to poly(glycolide) polymers. Internal fixation devices made from poly(lactide) have also been observed to exhibit an inflammatory reaction. Eitenmuller et al. reports that 9 of 19 patients (47.7%) who had fractures of the ankle treated with absorbable plates and screws of poly(lactide) had an inflammatory response. (J. Eitenmuller, A. David, A. Pomoner, and G. Muhyr: "Die Versorgung von Sprunggelenlzsfrakturen unter Verwendung von Platten und Schrauben aus resorbserbarem Polymermaterial", Read at Jahrestagung der Deutschen Gesellschaft fur Unfallheilkunde, Berlin, Nov. 22, 1989).

In vitro studies have been performed to monitor pH changes as well as weight loss and the appearance of lactic acid from screws fabricated from poly(lactide-co-glycolide) with a lactide:glycolide ratio of 85:15. (Vert et al., J. Controlled Release 16, 15–26 (1991)). An induction period of about ten weeks was observed before any significant change in media pH or weight loss occurred. This time period corresponds to the induction periods of seven to twenty weeks noted by clinicians. However, no attempt has been made to alleviate the source of inflammation.

BRIEF SUMMARY OF THE INVENTION

The invention is a bioerodible, or resorbable, implantable material, and devices made therefrom, comprising a bioerodible polymer that produces acidic products or low molecular weight resorbable fragments upon hydrolytic degradation, and a neutralization or buffering compound included in sufficiently high concentration to buffer the acidic products and maintain the local pH within a desired range or to decrease the rate of pH change as the implantable material degrades. The buffer compound incorporated into the material of the invention acts to neutralize the acidic degradation products which cause inflammatory foreign body response upon degradation of the bioerodible polymer. Thus, the invention reduces the sterile abscess condition that occurs in the bioerodible implant materials of the prior art.

Materials made according to the invention may be used for internal fixation devices (IFDs) for, e.g., the repair, replacement or reconstruction of damaged bone in any area of the body. For example, screws, pins and rods according to the invention are useful to hold bones together following surgery or to repair broken bones. An interbody spinal fusion device according to the invention can be used for spine repair. Bone graft devices according to the invention can be used to repair or reconstruct defects caused by surgery, tumors, trauma, implant revisions and infections, and also for joint fusion. Void filler devices according to the invention can be placed in the void created by removal of, e.g., a cyst or infected bone, or from trauma. A space-filling internal fixation device according to the invention can be prepared either ex situ or in situ, e.g., in the form of a space-filling, solidifying foam. Furthermore, IFDs according to the invention are also useful, e.g., as stents to separate or maintain the shape of blood vessels, as sutures or fibrous devices for incision repair, or for any other use that may benefit from the combination of a bioerodible polymer with a neutralization or buffering compound into an implantable internal fixation device.

The bioerodible materials and methods of the invention include a bioerodible polymer that forms acidic products as it degrades. The bioerodible polymer undergoes hydrolysis in the body and generates acidic products that cause irritation, inflammation, and swelling (sterile abscess formation) in the treated area. To counteract this effect, a neutralization compound, or buffer, is included in the bioerodible material to neutralize the acidic degradation products, or control the rate of pH decline, and thereby reduce the sterile abscess reaction. The neutralization compound included in the bioerodible material of the invention maintains the pH surrounding the area of surgery at approximately neutrality (i.e., pH 7), or any other pH chosen by the surgeon. Preferably, the pH is maintained in the range of 6–8, and more preferably in the range of 6.8–7.4. Alternatively, the neutralization compound controls the rate of acid production as the bioerodible material degrades, thereby serving to control the rate of pH decrease.

According to the invention, the bioerodible material includes a bioerodible polymer that undergoes hydrolysis to produce acidic products when exposed to an aqueous medium. In one preferred embodiment, the polymer poly (lactide-co-glycolide) (H[—OCHR—CO—]$_n$OH, R=H, CH$_3$) (PLGA) is used. The PLGA polymers used according to the invention have a lactide to glycolide ratio in the range of 0:100% to 100:0%, inclusive, i.e., the PLGA polymer can consist of 100% lactide, 100% glycolide, or any combination of lactide and glycolide residues. These polymers have the property of degrading hydrolytically to form lactic and glycolic acids. In another preferred embodiment, the bioerodible polymer is poly(propylene fumarate) (H[—O—CH(CH$_3$)—CH$_2$—O—CH=CH—CO—]$_n$OH), which may be desirably crosslinked using vinyl monomers such as vinyl pyrrolidone (VP). An advantage of VP crosslinking of PPF is that the crosslinks terminate at hydrolytically labile fumarate ester bonds, making the crosslinked network hydrolytically degradable. Furthermore, the hydrolysis products are highly soluble. Other bioerodible polymers useful in the invention include polydioxanone, poly(ε-caprolactone); polyanhydrides; poly(ortho esters); copoly(ether-esters); polyamides; polylactones; and combinations thereof.

The neutralization or buffering compound included in the bioerodible material of the invention may be any salt, base, base-containing or base-generating material that is capable of reacting with the acidic products generated upon hydrolysis of the bioerodible polymer. Exemplary buffering materials that may be implemented according to the invention include the salts of inorganic acids, the salts of organic acids, or the salts of polymeric organic acids. Preferably, the calcium salts of weak acids are used, such as calcium phosphate, although calcium carbonates, calcium acetates, calcium citrates and calcium succinates may also be used.

Polymeric buffers may also be used as buffering compounds according to the invention. Suitable polymeric buffers preferably include basic groups which neutralize the acidic products generated upon hydrolysis of the bioerodible polymer. Such polymeric buffers include hydrolyzable polyamines, hydrolytically stable polymers, such as poly(N-vinyl carbazole), poly(N-vinyl pyrrolidone), poly(acrylic acid), poly(acrylamide), or a copolymer based on acrylic acid.

Another class of buffering compounds useful in the materials and methods of the invention are compounds which, on exposure to water, hydrolyze to form a base as one reaction product. The generated base is free to neutralize the acidic products produced upon hydrolysis of the bioerodible polymer. Compounds of this type include aryl or alkyl carbamic acids and imines. The base-generating compounds used according to the invention offer the advantage that the rate of hydrolysis of the base generator may be selected to correlate to the rate of hydrolysis of the bioerodible polymer.

Preferably, the buffering compound has an acid dissociation constant that is smaller than the acid dissociation constant of the acidic products generated upon hydrolysis of the bioerodible polymer. Alternatively, the buffering compound preferably has a hydrolysis constant that is greater than the hydrolysis constant of the acidic products.

Preferably, the buffering compound included in the material of the invention is only partially soluble in an aqueous medium. In general, buffers of lower solubility are preferred because buffer loss from the polymer by diffusion will be minimized (Gresser and Sanderson, "Basis for Design of biodegradable Polymers for Sustained Release of Biologically Active Agents" in *Biopolymeric Controlled Release Systems*, Ch. 8, D. L. Wise, Ed., CRC Press, 1984).

In yet another embodiment, devices made from the bioerodible implantable material of the invention further include reinforcing fibers to enhance the structural properties thereof. These fibers may be made of polymeric material that is the same as or similar to the bioerodible material from which the device is made, from material that is the same as or similar to that of the neutralization compound or, alternatively, from another biocompatible polymer, which may be crosslinked with a suitable crosslinking agent to yield an interpenetrating network for increased strength and stability. In another alternative embodiment, the reinforcing fibers are incorporated into the device, e.g., during the molding process, being placed in the mold under tension and released after the process of molding is complete.

In another alternative embodiment, devices made from the bioerodible implantable material of the invention preferably include a biological growth factor, e.g., bone morphogenic protein, to enhance bone cell growth. The growth factor may simply be directly incorporated into the component formulation of a device. Alternatively, to protect the growth factor and to provide for controlled delivery, the biological growth factor may itself be compounded with a bioerodible, resorbable polymer in some of the many techniques available and prepared as a growth factor/polymer composite in pellet form, in small particle form or within the interstices or pores of a polymeric foam or low-density polymer. This polymer/growth factor composite may be incorporated directly into the component formulation or deposited into void spaces that have been created in the device.

Active bone cell material, e.g., periosteal cells or osteoblasts, may also be incorporated into a device, in order to facilitate bone cell growth. For example, the bone cells may first be incorporated into a biocompatible, bioerodible foam material and then deposited into void spaces of a device. In addition, a device made from the bioerodible implantable material of the invention may be prepared in such a manner as to exhibit a piezoelectric effect, to enhance bone wound healing.

The invention also includes methods of making a buffered bioerodible material for implantation into a surgical site. In one embodiment, the method according to the invention includes the steps of dissolving a bioerodible polymer in a solvent, and mixing a buffering compound with the dissolved bioerodible polymer, the buffering compound capable of buffering the acidic products within a desired pH range. The solvent is evaporated to produce a buffered bioerodible implantable material in film form. The resulting film may be further processed, for example, compacted under pressure, extruded through a die, injection molded, or shaped into a form useful for implantation.

In another embodiment, the method according to the invention includes mixing dry, solid bioerodible polymer particles of a specific size with dry, solid buffering compound particles of a specific size, and mixing the bioerodible polymer particles and the buffering compound particles in a desired proportion. This mixture may also be processed by, e.g., compacting, extrusion, injection molding, or shaping procedures.

In another embodiment, the method of the invention includes providing an open celled bioerodible foam polymer of controlled density and providing a buffer dissolved in a solvent wherein the foam polymer is not soluble in the solvent, such as described in U.S. Pat. No. 5,456,917 to Wise et al., the whole of which is incorporated by reference herein. The buffer is loaded into the foam polymer, and the loaded foam polymer is freeze dried to remove the solvent. The resulting loaded bioerodible polymer may be further ground into particles of a predetermined size, extruded through a die, or shaped into useful forms.

In another embodiment, the method of the invention includes providing a bioerodible polymer having a melting temperature and producing acidic products upon hydrolytic degradation, providing buffer particles comprising buffer material coated with a polymer having a melting temperature greater than the melting temperature of the bioerodible polymer. The bioerodible polymer is heated to a temperature between the melting temperatures of the bioerodible polymer and the coating polymer, and the heated bioerodible polymer is mixed with the coated buffer particles. The mixture is then cooled and processed into useful forms.

As used herein, the terms "resorbable" and "bioresorbable" are defined as the biologic elimination of the products of degradation by metabolism and/or excretion and the term "bioerodible" is defined as the susceptibility of a biomaterial to degradation over time, usually months. The terms "neutralization compound" or "buffer" are defined as any material that limits or moderates the rate of change of the pH in the implant and its near environment upon exposure to acid or base. The term "acidic products" is defined herein as any product that generates an aqueous solution with a pH less than 7.

BRIEF DESCRIPTION OF THE DRAWINGS

The invention will be more fully understood from the following detailed description taken in conjunction with the accompanying drawings in which.

DETAILED DESCRIPTION OF THE INVENTION

Figure 1A:
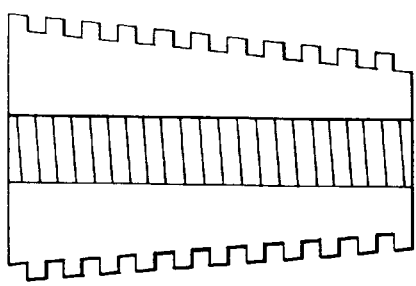
FIGS. 1A, 1B and 1C show internal fixation devices of the invention, in the form of a screw, a pin and a rod, respectively.
Figure 1B:
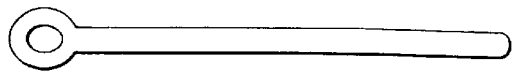
Figure 1C:
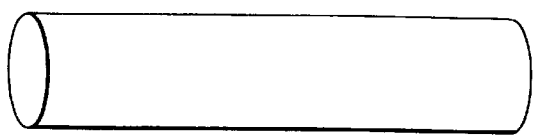
Figure 2:
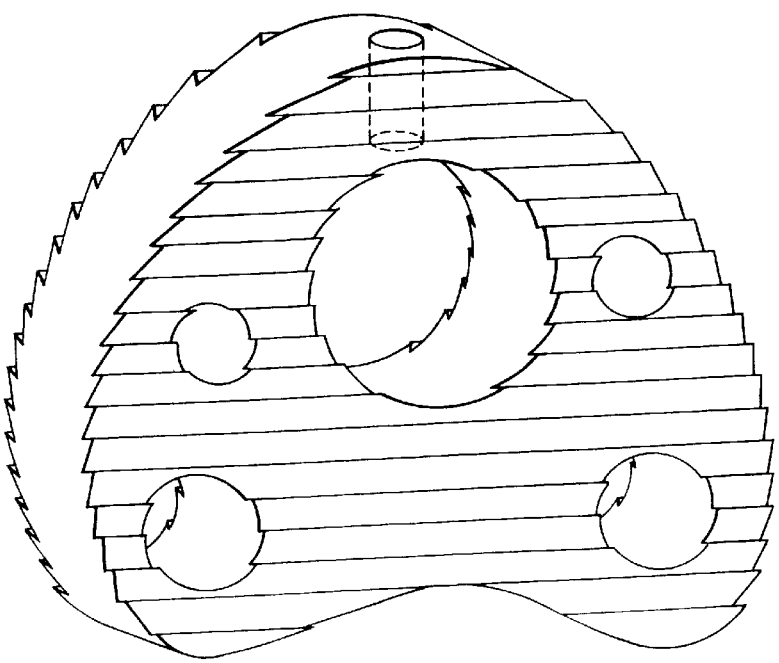
FIG. 2 shows an internal fixation device of the invention in the form of an interbody spinal fusion device.

The preferred embodiment of the invention relates to the field of internal fixation devices (IFDs) used for surgical repair, replacement or reconstruction of damaged bone in any area of the body. The conditions that can advantageously be corrected using an IFD of the invention include orthopaedic, maxillofacial, oral cranial or spinal injuries; or defects arising from tumor removal, trauma or other pathological events; or birth defects. For example, screws, pins and rods according to the invention, as depicted in FIGS. 1A–1C, are useful to hold bones together following surgery or to repair broken bones. An interbody spinal fusion device according to the invention, depicted in FIG. 2, can be used for spine repair.

Figure 3:
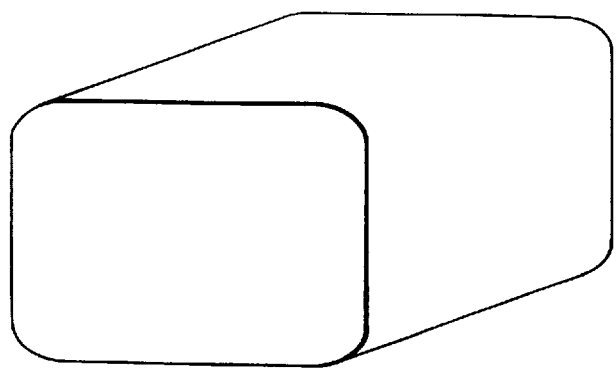
FIG. 3 shows an internal fixation device according to the invention in an early stage, before being formed into its final shape.
Figure 4:
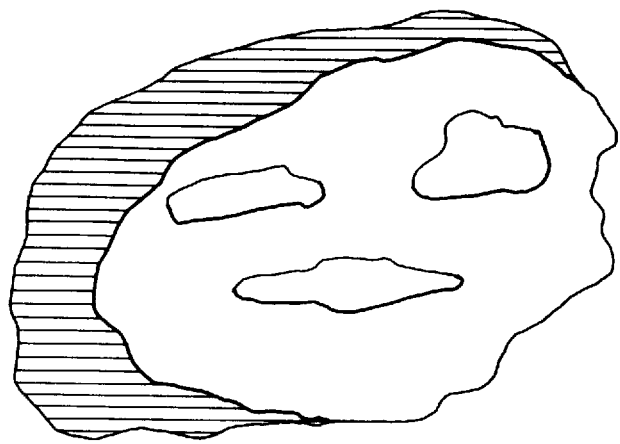
FIG. 4 shows an internal fixation device according to the invention in the form of a graft shaped to fit into a cranial defect.

In other embodiments, bone graft devices according to the invention can be prepared and used to repair or reconstruct defects caused by surgery, tumors, trauma, implant revisions and infections, and also for joint fusion. For example, a block of bioerodible material according to the invention, as depicted in FIG. 3, may be further machined according to the x-ray/CAD-CAM produced design of e.g., a cranial defect (see FIG. 4) or an intramedullary rod or a hip joint. The ex situ formed device may be further modified, as will be described below, and then surgically placed at the site of the in situ defect of the patient.

Figure 5:
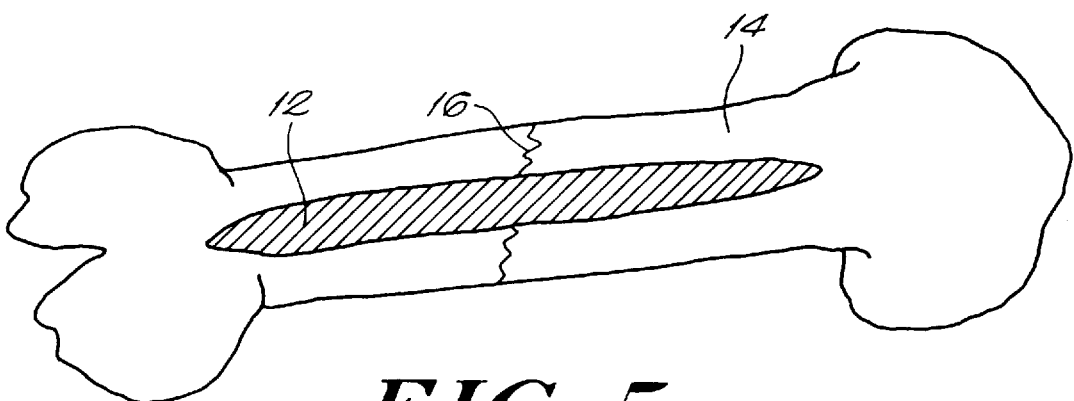
FIG. 5 shows a space filling internal fixation device according to the invention.

Alternatively, bone graft or space filling devices according to the invention can be placed in the void created by removal of, e.g., a cyst or infected bone, or from trauma. A space-filling internal fixation device according to the invention can be prepared either ex situ, as described above, or in situ, e.g., from a space-filling, solidifying foam. For example, referring to FIG. 5, a space filling device 12 is formed in place in the intramedulary space of a femur 14, across the area of a break 16.

The invention also includes a bioerodible, or resorbable, implantable material useful for making such internal fixation devices. The bioerodible, or resorbable, material comprises a bioerodible polymer capable of producing acidic products upon hydrolytic degradation and a buffering or neutralizing compound that buffers the acidic products within a desired pH range or decreases the rate of pH change as the bioerodible material degrades.

The bioerodible material of the invention includes at least one bioerodible polymer that undergoes hydrolysis to produce acidic products when exposed to an aqueous medium. The bioerodible polymers useful in the invention include, but are not limited to, polydioxanone (H[—O—CHR—CO—]$_n$OH); poly($\epsilon$-caprolactone); polyanhydride; poly (ortho ester); copoly(ether-ester); polyamide; polylactone; poly(propylene fumarate) (H[—O—CH(CH$_3$)—CH$_2$—O—CO—CH=CH—CO—]$_n$OH); poly(lactic acid); poly (glycolyic acid); poly(lactide-co-glycolide); and combinations thereof. Selection of a particular polymer is based primarily on the known properties of the polymer, such as the potentiality for cross-linking, polymer strength and moduli, rate of hydrolytic degradation, etc. One of ordinary skill in the art may take these and/or other properties into account in selecting a particular polymer for a particular application. Thus, the selection of a particular polymer is within the skills of the ordinary skilled practitioner.

In a preferred embodiment, the polymer poly(lactide-co-glycolide) (H[—OCHR—CO—]OH, R=H, CH$_3$) (PLGA) is used. The PLGA polymers used according to the invention desirably have a lactide to glycolide ratio in the range of 0:100% to 100:0%, inclusive, i.e., the PLGA polymer can consist of 100% L- or D,L-lactide (PLA), 100% glycolide (PGA), or any combination of lactide and glycolide residues. These polymers have the property of degrading hydrolytically in vivo to form organic acids (lactic acid and glycolic acid) which accumulate in the region surrounding an implant. These acids are metabolized and eventually excreted as carbon dioxide and water or enter the citric acid cycle.

The process by which alpha polyesters such as PLA, PGA, and PLGA biodegrade is primarily by non-specific hydrolytic scission of the ester bonds. The L-lactic acid that is generated when PLA or PLGA degrades becomes incorporated into the tricarboxylic acid cycle and is excreted from the lungs as carbon dioxide and water. Glycolic acid, produced both by random hydrolytic scission and by enzymatically mediated hydrolysis, may be excreted in the urine and also can enter the TCA cycle and eventually be oxidized to carbon dioxide and water (Hollinger et al., Clin. Orthop. Rel. Res. 207: 290–305, 1986).

A particularly preferred polymer for use in a device made from the bioerodible implantable material of the invention is poly(d,l-lactide-co-glycolide)-85:15 (Boehringer- Ingelheim: distributor, Henley Chemicals, Inc., Montvale, N.J.), the 85:15 designation referring to the lactide to glycolide mole ratio.

In another preferred embodiment, the bioerodible polymer is poly(propylene fumarate) (PPF) (H[—O—CH(CH$_3$)—CH$_2$—O—CH=CH—CO—]$_n$OH), which may be desirably crosslinked using vinyl monomers such as vinyl pyrrolidone (VP). An advantage of VP crosslinking of PPF is that the crosslinks terminate at hydrolytically labile fumarate ester bonds, making the crosslinked network hydrolytically degradable. Furthermore, the hydrolysis products are highly soluble. The crosslinking reaction should preferably seek to minimize homopolymer formation. Other crosslinking monomers such as methyl methacrylate (MMA) may also be used as long as bioerodibility is not compromised. A high PPF:VP ratio favors crosslinking; because the crosslinking reaction is carried out in solution, low concentrations of VP may be used. A crosslinking accelerator may also be included. The degree of crosslinking desirable will depend on the particular application, i.e., the relative hardness or rigidity desired in the finished device, but generally crosslinking of about 5% to 50% of the available crosslinking sites is acceptable, more particularly 5% to 30%.

The buffering or neutralizing compound included in the bioerodible material of the invention may be any salt, base, base-containing or base-generating material that is capable of reacting with the acidic products generated upon hydrolysis of the bioerodible polymer. Exemplary buffering materials include salts of inorganic or organic acids, salts of polymeric organic acids or polymeric bases such as polyamines. Preferably calcium salts of weak acids such as, e.g., the calcium phosphates (including the mineral hydroxyapatite) or calcium carbonate, are used as the buffering or neutralizing materials. To be useful, the conjugate acids from which the buffering materials are derived must have a pKa greater than those of L-lactic acid (pKa=3.79), D, L-lactic acid (pKa=3.86), or glycolic acid (pKa=3.83), if a PLGA is the polymer which is undergoing hydrolysis. Thus, for example, salts of acetic acid (pKa=4.74), or succinic acid (pK$_1$=4.19, pK$_2$=5.64) may also be used.

Buffer compositions of lower solubility are preferred because buffer loss from the polymer by diffusion will be slower (Gresser and Sanderson, supra). Preferably, the buffering compound has an acid dissociation constant that is smaller than the acid dissociation constant of the acidic products generated upon hydrolysis of the bioerodible polymer. Ionic buffers will, in general, be the salts of weak acids. The acid, of which the buffer is a salt, should have an ionization constant (acid dissociation constant, $K_a$) which is less than the $K_a$ for the acid products of polymer hydrolysis. Alternatively, the buffering compound has a hydrolysis constant that is greater than the hydrolysis constant of the acidic products.

Implementation of the concepts described above will now be describes using the buffering compound calcium carbonate as an example. Upon reaction with an acid, calcium carbonate forms a calcium salt and the weak acid carbonic acid ($H_2CO_3$). The carbonic acid undergoes decomposition to carbon dioxide ($CO_2$) and water ($H_2O$). The following sequence summarizes the reaction between calcium carbonate and an organic acid:

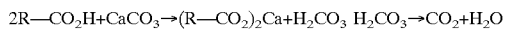

2R—CO$_2$H+CaCO$_3$→(R—CO$_2$)$_2$Ca+H$_2$CO$_3$   H$_2$CO$_3$→CO$_2$+H$_2$O

Gaseous carbon dioxide generated from the neutralization reaction is observed to be absorbed by the surrounding aqueous medium. The solubility of gaseous $CO_2$ in water at 760 mm Hg and 37° C. is approximately 0.95 mg/ml (Merck Index, 1989). Thus, upon being generated in situ, gaseous $CO_2$ dissolves in and is eliminated from tissue fluids. In addition, free acid generation from the polymers of the invention proceeds slowly. Thus, degradation of the polymer component is the rate limiting step in the reaction, and even during the period of most rapid degradation, generation of acidic products occurs slowly. The slow rate of degradation and associated acid production gives carbon dioxide ample time to dissolve in the surrounding fluids.

The amount of calcium carbonate required to be loaded into a bioerodible polymer matrix to neutralize a given quantity of lactic and glycolytic acids can be estimated by calculating the moles of monomeric acid produced at 100% hydrolysis. For PLGA of any composition (i.e., —[—O—CH(CH$_3$)—CO—]$_x$—[O—CH$_2$—CO—]$_{(1-x)}$, where x and (1−x) are the fractions of lactide and glycolide respectively, the molecular weight of the lactide component is 72 g/mol and the molecular weight of the glycolide component is 58 g/mol), the average monomer residue molecular weight is $$72x+58(1-x)=14x+58.$$

Thus, one gram of PLGA-50:50 (where x=0.5) will generate approximately 0.0154 moles of monomeric acid upon hydrolysis. Referring to the neutralization reaction above, the amount of calcium carbonate buffer needed to neutralize this quantity of acid is 0.0077 moles, or 0.77 grams (MW of $CaCO_3$=100 g/mol). Thus, the fraction of calcium carbonate buffer loaded into the polymer matrix is 43.5% by weight. Similar determinations can be calculated for other polymer and buffer combinations and are within the skills of the ordinary skilled practitioner. Other calculations may also be made, for example, calculation of the amount of buffer required to neutralize a percentage of the acid groups generated upon hydrolysis.

An appropriate buffer should have a low aqueous solubility so that it will not be rapidly lost by dissolution. The basic component of the buffer (the anion) should react easily with the protons of the acid products of hydrolysis. Letting $B^-$ represent the buffer anion and $L^-$ the lactate (or glycolic) anion, the equilibrium can be expressed as:

$$HL+B^- \leftrightarrows L^- +HB$$

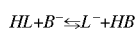

In other words, HB must be a weaker acid than HL (or $B^-$ must be a stronger base than $L^-$). These relationships may be expressed quantitatively by ionization constants of the respective acids (Ka):

$$Ka^{HB} < Ka^{HL}$$

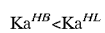

Using the buffer CaHPO$_4$ (dibasic calcium phosphate) as an example, the reaction of lactic acid with the anion HPO$_4^{-2}$ is:

$$HL+HPO_4^{-2} \leftrightarrows L^- +H_2PO_4^-$$

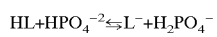

The H$_2$PO$_4^-$ anion has an acid dissociation constant of approximately 6.31×10$^{-8}$ whereas the various racemates of lactic acid have dissociation constants in the range of approximately 1.38×10$^{-4}$ to 1.62×10$^{-4}$. Taking 1.5×10$^{-4}$ as a mean value, the equilibrium constant for the above reaction may be calculated as:

$$K_{eq} = \frac{K_a^{HL}}{K_a^{H_2PO_4}} = 2.4 \times 10^3$$

Thus, the equilibrium lies to the right and protons produced by ionization of lactic or glycolic acids will be removed by the buffer.

Alternatively, a preferred buffering compound is hydroxyapatite. The formula for hydroxyapatite, $Ca_{10}(OH)_2(PO_4)_6$, may be written as $Ca(OH)_2 \cdot 3Ca_3(PO_4)_2$. When written in this manner it is seen that the following neutralization reactions may be written:

$2RCO_2H + Ca(OH)_2 \cdot 3Ca_3(PO_4)_2 \rightarrow 2RCO_2^- + Ca^{+2} + 2H_2O + 3Ca_3(PO_4)_2$ $12RCO_2H + 3Ca_3(PO_4)_2 \rightarrow 6H_2PO_4 + 9Ca^{+2} + 12RCO_2^-$ The dissociation constant of water (the conjugate acid of the hydroxyl ion) is $K_w = 10^{-14}$. The basic phosphate ion, $PO_4^{-3}$, can neutralize two protons forming the following acids, for which dissociation constants are given:

$RCO_2H + PO_4^{-3} \rightarrow RCO_2^- + HPO_4^{-2}$ $RCO_2H + HPO_4^{-2} \rightarrow RCO_2^- + H_2PO_4$ $K_2$ of $H_2PO_4^{-1} = 6.2 \times 10^{-8}$ $K_3$ of $HPO_4^{-2} = 4.2 \times 10^{-13}$ While all of the buffering or neutralization compounds described can ameliorate the rate of decline in pH in the region of polymer hydrolysis, the use of hydroxyapatite as a neutralization compound also supports osteoconductivity and, thus, promotes bony ingrowth, obviating loosening of an implanted device. A bioerodible, resorbable implanted device with such properties could provide structural support to stabilize the area requiring healing over the period of time required for natural healing to occur.

Buffers included in the polymer in solid form preferably should have a relatively small particle size, for example, between 1.0 and 250 μm. Particle size reduction can be accomplished by any standard means known in the art, such as ball milling, hammer milling, air milling, etc. If buffer and polymer are to be blended by the dry mixing method (described below), the polymer particle size must also be considered. Polymers such as the PLGAs have relatively low glass transition temperatures and melting temperatures. Thus, polymer particle size reduction must be accompanied by cooling, for example using a Tekmar A-10 mill with a cryogenic attachment.

Following milling, the desired particle size range of the buffer and the polymer may be recovered by sieving through, for example, U.S. Standard sieves. Particles in the size ranges of <45, 45–90, 90–125, 125–180, 180–250 μm may be conveniently isolated.

In selection of particle size range, it is sometimes desirable to combine two or more ranges, or to use a wide range of sizes, for instance all sizes less than 250 μm. Larger particles may be preferred in some applications of the invention because larger particles take longer to be eroded by the acids and will therefore extend the useful lifetime of the buffer. In some cases particle size reduction will not be necessary, such as when commercially available precipitated calcium carbonate is used (e.g., Fisher Scientific, Inc., Catalog No. C-63).

The effectiveness of the buffering or neutralization substances described above in neutralizing the acid products of polymer hydrolysis depends not only on the quantity of the substance present in the matrix, but also on particle size and distribution, total surface area in contact with the polymer, and solubility. Each of these parameters may be controlled by methods chosen for preparation of the substance.

The inclusion of soluble materials such as citric acid with a sodium bicarbonate, calcium acetate or calcium gluconate compound also has an important second function in vivo. Upon exposure to aqueous media such as tissue fluids these compounds dissolve almost immediately, leaving pores in the material of the invention. These pores facilitate bone cell migration into a device prepared from the material of the invention, and thus serve as osteoconductive pathways for bone healing. Pore size may be controlled by controlling the size of the soluble material introduced to the material of the device. The combination of citric acid and sodium bicarbonate is particularly useful in material for a void filler device, which is formed while it has a putty-like consistency and then solidifies into the desired final shape. As carbon dioxide and water are formed in vivo upon exposure of the citric acid and sodium bicarbonate combination in the device to tissue fluids, the released carbon dioxide gas will form bubbles or "designed holes" in the ultimately cured filler device, in place of the solid chemical.

The presence of calcium ions in the buffered device has advantages with respect to the physical properties of the device as it undergoes erosion. It has been shown that calcium ions form ionic bridges between carboxylate terminal polymer chains (Domb et al., J. Polymer Sci. A28, 973–985 (1990); U.S. Pat. No. 4,888,413 to Domb). Calcium ion bridges between carboxylate anions increase the strength of composites in which the polymer chains are terminated by carboxylate anion end groups over similar chains terminated by the hydroxyl groups of, e.g., terminal glycol moieties or terminal α-hydroxy acids. In an analogous manner, the polyesters comprising the family of PLGA's are expected to be strengthened by calcium bridges between carboxylate anion terminated chains.

In addition to organic or inorganic salts which can serve as buffers, polymeric buffers may also be implemented in the materials and methods of the invention. Polymeric buffers useful in the invention preferably include at least one basic group which is capable of neutralizing the acidic products generated upon hydrolysis of the bioerodible polymer. As used herein, the term "base" and "basic group" is defined as any chemical group capable of donating an electron pair. The basic groups of the polymeric buffer may be attached to substituents pendant to the polymeric buffer backbone, or may be attached directly to the polymer backbone, or may be included as part of the polymer backbone itself. The polymers serving as buffers may be stable to hydrolysis, such as "addition" or "vinyl-type" polymers, i.e., those polymers formed by polymerization of monomers containing carbon-carbon double bonds (substituted ethylenes) to form a chain of repeating units in which the repeating unit has the same composition as the monomer. Alternatively, the buffering polymers may themselves be subject to hydrolytic action, such as "condensation" or "step" polymers, i.e., those polymers formed from polyfunctional monomers with loss of material at each step. Examples of useful condensation polymers are polyesters and polyamides.

As with buffering compounds, the negative ions of the polymeric buffers act as bases which neutralize the acids produced by hydrolysis of bioerodible polymer. A generalized structure of an exemplary polymeric buffer is shown below. In the following diagram, M represents the monomeric units which form the buffer polymer backbone, and R represents a hydrogen atom, an alkyl group or an aryl group.

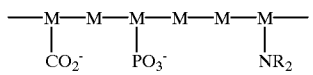

As shown in the diagram, the monomeric units M may have An substituents which bear basic groups, such as carboxyl, amine, or phosphonate groups. Each monomeric unit may bear a basic group, but this is not a necessary requirement. In addition, the basic groups of a given polymeric molecule may not all be the same. As shown in the diagram above, carboxyl, amine or phosphonate groups may be used alone, or in combination. Moreover, some polymeric buffers may be synthesized from two or more monomers so that in a given polymeric buffer, the M groups differ.

Thus, according to the invention, many polymeric buffers may be selected based on properties such as buffering capacity and pKa value. An important parameter in choosing a polymeric buffer is that the pKa of the acid formed by the polymeric buffer be less than the pKa of the hydrolysis products of the bioerodible polymer. Exemplary polymeric buffers include, but are not limited to, hydrolyzable polyamines, such as poly(aspartic acid), poly(glutamic acid), poly(lysine), poly(amino-γ-benzyl glutamate); hydrolytically stable polymers (vinyl or addition polymers), such as poly(N-vinyl carbazole), poly(N-vinyl pyrrolidone), poly(acrylic acid), poly(acrylamide), or a copolymer based on acrylic acid, such as

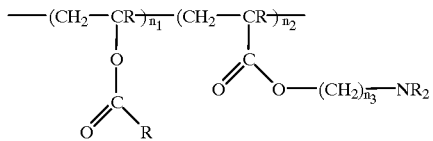

where R=H, alkyl, or aryl, (R groups need not be identical). In copolymers, such as copolymers of acrylic acid, the residue monomer units forming the backbone may be distributed randomly or may occur in sequential blocks (random or block copolymers). Hydrolyzable polyesters of the general structure

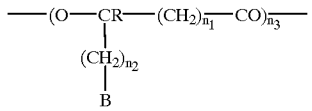

may also be used. In the structures shown above, R=H, alkyl, or aryl; $n_1$ and $n_2 \geq 0$; $n_3 \geq 3$; B=a basic group, such as —$CO_2$—, —$NR_2$, or —$PO_3R^-$.

In an alternative embodiment, the basic group of the polymeric buffer may be covalently bonded within the monomeric unit. An example of this type of polymeric buffer is poly(ethylamine)-($CH_2$—$CH_2$—NH)$_n$—.

Another class of buffer compounds useful in the invention are compounds which, on exposure to water, hydrolyze to form a base as one reaction product. The generated base is free to neutralize the acidic products produced upon hydrolysis of the bioerodible polymer. Compounds of this type include aryl or alkyl carbamic acids and imines. These "base-generating compounds" offer the advantage that the rate of hydrolysis of the base generator may be selected to correlate to the rate of hydrolysis of the bioerodible polymer.

Thus, in one embodiment, compounds such as aryl and alkyl carbamic acids may be implemented as follows to generate the basic compounds that act as buffers. The hydrolysis reaction which results in base generation is:

The carbonic acid generated during the reaction is in equilibrium with carbon dioxide and water:

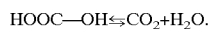

The basic product $H_2NR$ reacts with the acid products of bioerodible polymer hydrolysis in a neutralization reaction. In one embodiment, the hydrolysis products of poly(lactide-co-glycolide) (hereinafter designated as HL) may be neutralized by the generated base:

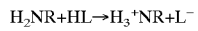

In an alternative embodiment, imines may also be used to generate bases on hydrolysis according to the general equation:

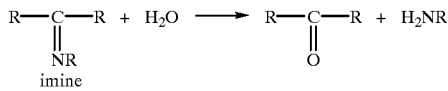

The groups labelled R above may be a hydrogen atom, an alkyl group, or an aryl group.

Following protonation of the imine nitrogen, hydrolysis proceeds by nucleophilic attack by water at the carbon atom of the C=N bond. This process is facilitated by electron withdrawing groups attached to the nitrogen. Such substituents would thus increase the rate of hydrolysis. Conversely, the rate of hydrolysis would be diminished by electron donating substituents on the carbon and an electron withdrawing group on the nitrogen. Bulky groups, such as long alkyl substituents would tend to offer steric hindrance to the approach of the water molecules and thus would suppress the hydrolysis rate. Accordingly, by appropriate choice of R, the rate of hydrolysis of the imine may be either increased or decreased. This characteristic of base generating compounds is advantageous in that the rate of hydrolysis of the base generator may be selected to correlate to the rate of hydrolysis of the bioerodible polymer. Thus, in a given period of time, the quantity of base formed from the base generating compound will be equivalent to the quantity of acidic products formed by bioerodible polymer hydrolysis, and the stoichiometry of the reaction will be in the correct proportions to neutralize the appropriate amount of acid to maintain the pH within the desired range.

Several methods may be used to incorporate the buffer into the polymer. These methods include solution casting coupled with solvent evaporation, dry mixing, incorporating the buffer into a polymer foam, and the polymer melt method.

Method 1. Solution Casting—Solvent Evaporation

This method may be used with buffers which are either soluble or insoluble in the solvent. The bioerodible polymer is dissolved in any suitable volatile solvent, such as acetone, tetrahydrofuran (THF), methylene chloride or liquid carbon dioxide (i.e., carbon dioxide under super critical conditions). The buffer, which may be soluble or insoluble in this solvent, is added to give the final desired ratio of polymer to buffer. If particle size reduction of the buffer is necessary, it may be accomplished by ball milling the suspension of buffer in the polymer solution. In contrast, if the buffer is soluble in the chosen solvent, particle size reduction at any stage is not necessary.

The suspension or co-solution is cast as a film on a glass or other inert surface, and the solvent is removed by air drying. Residual solvent remaining in the film may be further removed by subjecting the film to vacuum drying at elevated temperatures. As an example, if calcium carbonate is to be used as a buffering compound and it is desired to neutralize 50% of the acid formed by hydrolysis of PLGA-50:50, the buffer content of the composition should be 27.8%.

In an exemplary embodiment, to prepare 50 grams of composite, 36.1 grams of PLGA-50:50 are dissolved in approximately 250 ml of tetrahydrofuran, and 13.9 grams of calcium carbonate of the desired particle size range is added to the solution mixture. After distributing the calcium carbonate homogeneously by mixing, the suspension is dried to a film as described above.

The resulting film may be processed by compaction under high pressure, extruded through a die, injection molded, or other method known in the art. Further definition of the final shape may be accomplished at this point by any desirable machining process, such as lathing.

Method 2. Dry-Mixing

A polymer of appropriate particle size range is mixed with the buffer, also of chosen particle size range, in proportions to give the desired stoichiometric buffering capacity. The dry mixture is thoroughly blended by rotating the mixture in a ball mill jar from which the grinding balls have been omitted, or other suitable mixing device. The blended mixture may then be processed by compaction, extrusion, injection molding, etc., as described above.

Method 3. Incorporating the Buffer into a Polymer Foam

This method deposits the buffer as microcrystals within the pores of a foamed polymer. An open celled polymer foam of controlled density may be formed by lyophilization of a polymer solution as described in U.S. Pat. No. 5,456,917 to Wise et al., the whole of which is incorporated by reference herein. For example, open celled PLGA-85:15 foams (i.e., foams with 85% lactide and 15% glycolide by weight) with different morphologies are created by lyophilization of frozen solutions of the polymer from either benzene or glacial acetic acid. The density and void volume of the foam is a function of the initial polymer solution as shown in TABLE 1.

TABLE 1

FOAM DENSITY AS A FUNCTION OF SOLUTION CONCENTRATION

| Concentration of solution, mg/ml | Average Density of Foam, mg/cm$_3$ |
|---|---|
| 30.0 | 43.0 |
| 40.0 | 60.1 |
| 45.0 | 65.0 |
| 50.0 | 70.1 |
| 66.7 | 87.5 |

In this method, buffers which are soluble in a solvent which does not dissolve the polymer foam are preferred, such as water soluble buffers or low molecular weight alcohols, such as ethanol. The weight fraction of the buffer in the polymer/buffer composite, f, will depend on both absolute density of the polymer, $d_p$, the density of the foam, $d_f$, and the concentration of the buffer in the solvent, C. This dependency is given by the loading equation:

$$f=[1+d_f d_p/C(d_p-d_f)]^{-1}$$

A buffer solution comprising a chosen buffer in a suitable solvent is forced into the pores of the open celled foam by repeated cycles of evacuation (degassing) and repressurization (by emitting air at atmospheric pressure or higher). After the foam has been impregnated with the buffer solution, the saturated foam is subjected to a second lyophilization to remove the solvent. Following this loading process, the polymer/buffer composite may be processed as described above.

Method 4. Polymer Melt

A known weight of the buffer is incorporated by mixing into a known weight of a suitable melted polymer. A quantity of polymer is heated to a temperature above its melting point, and a suitable buffer is blended into the melted polymer. The resulting polymer/buffer composite is solidified by cooling, and may be processed as described above, or ground and sieved prior to processing.

In some applications, it may be desirable to protect the buffering compound, for example, during processing according to the melt method, or to make the buffering compound available at the later stages of polymer degradation. In such cases, it is desirable to coat the buffering compound particles with a material that degrades at a slower rate than the material chosen for the fixation devices. Thus, the buffering compound is exposed only after the body of the device and the coating material have partially degraded. Exemplary materials used to coat the buffering compound particles include high molecular weight poly(L-lactide) or poly($\epsilon$-caprolactone).

The particles of buffering compound may be coated with the protective material by any method that coats particles, such as spray coating with a solution of protecting polymer or micro-encapsulation. Alternatively, a chosen protective polymer may be made in a melted state and buffer particles are added. The melt is cooled and ground and milled to the desired particle size range. Alternatively, the buffering compound may be added to a solution of the protective polymer and removing the solvent by evaporation. The dried mass is compacted in a mold under high pressure and grinding or milling the compacted mass to the appropriate particle size range.

Although PLGA polymers are used in the preceding examples, one of ordinary skill in the art will appreciate that other polymers, such as polydioxanone, poly($\epsilon$-caprolactone); polyanhydrides; poly(ortho esters); copoly (ether-esters); polyamides; polylactones; poly(propylene fumarates); and combinations thereof, may be similarly processed according to the methods of the invention. Moreover, selection of a particular polymer is based primarily on the known properties of the polymer such as the degree of cross-linking, polymer strength, polymerization rate, rate of hydrolytic degradation, etc. One of ordinary skill in the art may take these and/or other properties into account in selecting and processing a particular polymer for a particular application. Thus, the selection of a particular bioerodible polymer and the selection of the best method for incorporating a buffering or neutralization compound into the chosen polymer is within the skills of the ordinary skilled practitioner.

A device incorporating the bioerodible, or resorbable, implantable material of the invention optionally includes a biological growth factor, e.g., bone morphogenic protein, to enhance bone cell growth. The growth factor may simply be directly incorporated into the component formulation of the device. Alternatively, to protect the growth factor and to provide for controlled delivery, the biological growth factor may be itself compounded with a bioerodible polymer by one of the many techniques available and prepared as a growth factor/polymer composite in pellet form, in small particle form or within the interstices or pores of a polymeric foam or low-density polymer. This polymer/growth factor composite may be incorporated directly into the composite formulation or deposited into void spaces created in the device.

Active bone cell material, e.g., periosteal cells, osteoblasts or other bony cells, may also be incorporated with a device, e.g., in a foam surrounding, or deposited in, the device, so that the cells may facilitate bone cell fusion. To carry out such an incorporation, the periosteum surrounding a human bone is removed and cultured following standard cell culturing techniques. The scaffold for such periosteal cell growth is a resorbable polymer foam or mesh. This scaffolding is prepared by dipping the completed device in a polymer/solvent (such as PLGA dissolved in acetic acid). The so-wetted device is then frozen and subsequently freeze-dried (lyophilized) resulting in a foam layer (or coating) of polymer surrounding the device. After the periosteal cells have been grown in this foam layer, the device is incorporated into the site of the body needing repair.

In another embodiment, the device may be prepared in such a manner as to exhibit a piezoelectric effect. It is known that oriented (molecularly aligned) biopolymers such as PLGA have piezoelectric characteristics. In addition, the oriented biopolymer poly-l-lactic acid (PLLA) has been shown to promote bone wound healing (Shimono et al., *In Vivo* 10:471–476, 1996 and Ikada et al., J. Biomed, Mater. Res. 30:553–558, 1996). To take advantage of this phenomenon, the bioerodible polymer material is first aligned, by drawing, for example, such that all polymer chains are essentially parallel. The device is then cut from this aligned polymeric material such that the polymer chains are at approximately a 45° angle to the surface of the device, this angle being known to produce the optimal piezoelectric effect.

A device incorporating the bioerodible, or resorbable, implantable material of the invention, such as a PLGA implant, can be effectively reinforced by the use of degradable scaffolds which are molecularly dispersed in the host, e.g., PLGA, polymer. For example, a mixture containing PLGA, poly(propylene fumarate)(PPF), and vinyl pyrrolidinone(VP) as a crosslinking agent (or other vinyl monomer) may be combined with an initiator (such as benzoyl peroxide). The PPF chains are crosslinked by VP to form an interpenetrating network of crosslinked PPF and PLGA polymer chains. Further crosslinking is possible using γ-irradiation, e.g. 2.5 mrad.

Several reinforcement techniques described in the literature include self-reinforcement using aligned PLGA fibers (Vainionpaa et al., Biomaterial 8:46–48, 1987; Pihlajamaki et al., J. Bone and Joint Surgery 74:13:853–857, 1992; Ashammakhi et al., J. Biomedical Materials Research 29: 687–694, 1995) and reinforcement with calcium phosphate glass fibers (R. A. Casper et al., Polym. Mater. Sci. Eng. 53:497–501, 1985).

Reinforcement can also be achieved by molding the device first as a rod of rectangular or other suitable cross-section that contains fibers under tension, as described in co-pending U.S. application Ser. No. 09/131,716, which is hereby incorporated by reference herein.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

We claim:
1. An internal fixation device comprising:
a bioerodible implantable material, said material comprising
a bioerodible polymer, said bioerodible polymer producing acidic products or low molecular weight resorbable fragments upon hydrolytic degradation; and
a buffering or neutralizing agent in sufficiently high concentration to moderate the rate of change of pH of said bioerodible material during bioerosion, comprising 25–100% resorbable material.

2. An internal fixation device comprising:
a bioerodible implantable material, said material comprising
a bioerodible polymer, said bioerodable polymer producing acidic products or low molecular weight resorbable fragments upon hydrolytic degradation; and
a buffering or neutralizing agent in sufficiently high concentration to moderate the rate of change of pH of said bioerodible material during bioerosion, wherein the parent acid of said buffering or neutralizing agent has an acid dissociation constant that is smaller than the acid dissociation constant of said acidic products.

3. An internal fixation device comprising:
a bioerodible implantable material, said material comprising
a bioerodible polymer, said bioerodible polymer producing acidic products or low molecular weight resorbable fragments upon hydrolytic degradation; and
a buffering or neutralizing agent in sufficiently high concentration to moderate the rate of change of pH of said bioerodible material during bioerosion, wherein said buffering or neutralizing agent has a hydrolysis constant that is greater than the hydrolysis constant of said acidic products.

4. An internal fixation device comprising:
a bioerodible implantable material, said material comprising
a bioerodible polymer, said bioerodible polymer producing acidic products or low molecular weight resorbable fragments upon hydrolytic degradation; and
a buffering or neutralizing agent in sufficiently high concentration to moderate the rate of change of pH of said bioerodible material during bioerosion, wherein said bioerodible, implantable material further comprises a salt selected from the group consisting of acetates, succinates and citrates.

5. An internal fixation device comprising:
a bioerodible implantable material, said material comprising
a bioerodible polymer, said bioerodible polymer producing acidic products or low molecular weight resorbable fragments upon hydrolytic degradation; and
a buffering or neutralizing agent in sufficiently high concentration to moderate the rate of change of pH of said bioerodible material during bioerosion, wherein said bioerodible, implantable material further comprises citric acid and sodium bicarbonate.

6. An internal fixation device comprising:
a bioerodible implantable material, said material comprising:

a bioerodible polymer, said bioerodible polymer producing acidic products or low molecular weight resorbable fragments upon hydrolytic degradation; and a buffering or neutralizing agent in sufficiently high concentration to moderate the rate of change of pH of said bioerodible material during bioerosion, wherein said bioerodible, implantable material further comprises reinforcing fibers.

7. The internal fixation device of claim 6, wherein said reinforcing fibers are made of a material that is the same as or similar to said bioerodible polymer.

8. The internal fixation device of claim 1, wherein said bioerodible polymer comprises poly(propylene fumarate).

9. An internal fixation device comprising:

a bioerodible implantable material, said material comprising a bioerodible polymer, said bioerodible polymer producing acidic products or low molecular weight resorbable fragments upon hydrolytic degradation; and a buffering or neutralizing agent in sufficiently high concentration to moderate the rate of change of pH of said bioerodible material during bioerosion, wherein said bioerodible implantable material further comprises bony cells.

10. The internal fixation device of claim 1, wherein said buffering or neutralizing agent is the salt of an organic acid.

11. The internal fixation device of claim 1, wherein said buffering or neutralizing agent is a polymer comprising at least one basic group.

12. An internal fixation device comprising:

a bioerodible implantable material, said material comprising a bioerodible polymer, said bioerodible polymer producing acidic products or low molecular weight resorbable fragments upon hydrolytic degradation; and a buffering or neutralizing agent in sufficiently high concentration to moderate the rate of change of pH of said bioerodible material during bioerosion, wherein said device has been treated to comprise void spaces.

13. The internal fixation device claim 11, wherein said at least one basic group is covalently bonded within said polymer.

14. An internal fixation device comprising:

a bioerodible implantable material, said material comprising a bioerodible polymer, said bioerodible polymer producing acidic products or low molecular weight resorbable fragments upon hydrolytic degradation; and a buffering or neutralizing agent in sufficiently high concentration to moderate the rate of change of pH of said bioerodible material during bioerosion, wherein molecular chains of said bioerodible polymer have been aligned to be essentially parallel and wherein said device has been prepared such that the aligned molecular chains of said polymer are at approximately a 45° angle to a surface of said device.

15. A bioerodible implantable material, said material comprising a bioerodible polymer, said bioerodible polymer producing acidic products or low molecular weight resorbable fragments upon hydrolytic degradation; and a buffering or neutralizing agent in sufficiently high concentration to moderate the rate of change of pH of said bioerodible material during bioerosion, wherein the parent acid of said buffering or neutralizing agent has an acid dissociation constant that is smaller than the acid dissociation constant of said acidic products.

16. A bioerodible implantable material, said material comprising a bioerodible polymer, said bioerodible polymer producing acidic products or low molecular weight resorbable fragments upon hydrolytic degradation; and a buffering or neutralizing agent in sufficiently high concentration to moderate the rate of change of pH of said bioerodible material during bioerosion, wherein said buffering or neutralizing agent has a hydrolysis constant that is greater than the hydrolysis constant of said acidic products.

17. A bioerodible implantable material, said material comprising a bioerodible polymer, said bioerodible polymer producing acidic products or low molecular weight resorbable fragments upon hydrolytic degradation;

a buffering or neutralizing agent in sufficiently high concentration to moderate the rate of change of pH of said bioerodible material during bioerosion; and a salt selected from the group consisting of acetates, succinates and citrates.

18. A bioerodible implantable material, said material comprising a bioerodible polymer, said bioerodible polymer producing acidic products or low molecular weight resorbable fragments upon hydrolytic degradation;

a buffering or neutralizing agent in sufficiently high concentration to moderate the rate of change of pH of said bioerodible material during bioerosion; and a combination of citric acid and sodium bicarbonate.

19. A bioerodible implantable material, said material comprising a bioerodible polymer, said bioerodible polymer producing acidic products or low molecular weight resorbable fragments upon hydrolytic degradation;

a buffering or neutralizing agent in sufficiently high concentration to moderate the rate of change of pH of said bioerodible material during bioerosion; and reinforcing fibers.

20. The bioerodible implantable material of claim 19, wherein said reinforcing fibers are made of a material that is the same as or similar to said bioerodible polymer.

21. The bioerodible implantable material of claim 19, wherein said reinforcing fibers are made of a material that is the same as or similar to said buffering or neutralizing agent.

22. A bioerodible implantable material, said material comprising a bioerodible polymer, said bioerodible polymer producing acidic products or low molecular weight resorbable fragments upon hydrolytic degradation;

a buffering or neutralizing agent in sufficiently high concentration to moderate the rate of change of pH of said bioerodible material during bioerosion; and bony cells.

23. The bioerodible implantable material of claim 22, wherein said bony cells comprise perosteal cells.

24. The bioerodible implantable material of claim 22, wherein said bony cells comprise osteoblasts.

* * * * *

UNITED STATES PATENT AND TRADEMARK OFFICE
CERTIFICATE OF CORRECTION

PATENT NO.         : 6,419,945 B1
APPLICATION NO.    : 09/166508
DATED              : July 16, 2002
INVENTOR(S)        : Joseph D. Gresser et al.

It is certified that error appears in the above-identified patent and that said Letters Patent is hereby corrected as shown below:

Column 6, line 41, " (H [—OCHR—CO] OH, " should read as follows:
-- (H [—OCHR—CO—] $_n$OH, -- ;

Column 9, line 11, "$Ca(OH)_2 \cdot 3Ca_3(PO_4)_2$" should read as follows:
--$Ca(OH)_2 \bullet 3Ca_3(PO_4)_2$-- ;

Column 9, line 15, "$2RCO_2H + Ca(OH)_2 \cdot 3Ca_3(PO_4)_2 \rightarrow 2RCO_2^- + Ca^{+2} + 2H_2O +$" should read -- $2RCO_2H + Ca(OH)_2 \bullet 3Ca_3(PO_4)_2 \rightarrow 2RCO_2^- + Ca^{+2} + 2H_2O +$ --;

Column 11, line 8, delete "An" ;

Column 16, line 16, "bioerodable" should be --bierodible-- ;

Column 17, lines 13-14, delete the entire claim 8 and insert the following claim 8 :

--8. The internal fixation device of claim 6, wherein said reinforcing fibers are made of a material that is the same as or similar to said buffering or neutralizing agent. --;

Column 17, lines 27-28, delete the entire claim 10 and insert the following claim 8 :

--10. The internal fixation device of claim 9, wherein said bony cells comprise perosteal cells.--;

Column 17, lines 29-31, delete the entire claim 11 and insert the following claim 11 :

--11. The internal fixation device of claim 9, wherein said bony cells comprise osteoblasts.-- ;

UNITED STATES PATENT AND TRADEMARK OFFICE
CERTIFICATE OF CORRECTION

PATENT NO. : 6,419,945 B1
APPLICATION NO. : 09/166508
DATED : July 16, 2002
INVENTOR(S) : Joseph D. Gresser et al.

It is certified that error appears in the above-identified patent and that said Letters Patent is hereby corrected as shown below:

Column 17, lines 44-46, delete the entire claim 13 and insert the following claim 13 :

--13. The internal fixation device of claim 12, wherein said device has been treated to comprise void spaces of a defined size. -- .

Column 17, line 56, "delete "and" ;

Signed and Sealed this

Second Day of January, 2007

JON W. DUDAS
*Director of the United States Patent and Trademark Office*